(12) United States Patent
Oka et al.

(10) Patent No.: US 10,533,967 B2
(45) Date of Patent: Jan. 14, 2020

(54) ELECTROPHORETIC SUPPORT BODY AND ELECTROPHORETIC DEVICE

(71) Applicant: Panasonic Intellectual Property Management Co., Ltd., Osaka (JP)

(72) Inventors: Hiroaki Oka, Osaka (JP); Takeshi Yanagida, Fukuoka (JP); Nobuhiro Hayashi, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 167 days.

(21) Appl. No.: 15/558,539

(22) PCT Filed: Mar. 25, 2016

(86) PCT No.: PCT/JP2016/001735
§ 371 (c)(1),
(2) Date: Sep. 14, 2017

(87) PCT Pub. No.: WO2016/163097
PCT Pub. Date: Oct. 13, 2016

(65) Prior Publication Data
US 2018/0074014 A1  Mar. 15, 2018

(30) Foreign Application Priority Data
Apr. 10, 2015 (JP) ................. 2015-080490

(51) Int. Cl.
*G01N 27/447* (2006.01)
(52) U.S. Cl.
CPC .  *G01N 27/44795* (2013.01); *G01N 27/44721* (2013.01); *G01N 27/44773* (2013.01)
(58) Field of Classification Search
CPC .......... G01N 27/447–44795; B01D 57/00–02; C02F 1/4696; B81B 1/00–008
See application file for complete search history.

(56) References Cited

U.S. PATENT DOCUMENTS

| 4,443,319 A | 4/1984 | Chait et al. |
| 5,587,062 A * | 12/1996 | Togawa ........... G01N 27/44739 204/456 |

(Continued)

FOREIGN PATENT DOCUMENTS

| EP | 1930721 A2 | 6/2008 |
| JP | 2004-361393 | 12/2004 |

(Continued)

OTHER PUBLICATIONS

Machine English translation for JP2004361393 (Year: 2004).*

(Continued)

*Primary Examiner* — Bach T Dinh
(74) *Attorney, Agent, or Firm* — McDermott Will & Emery LLP

(57) ABSTRACT

An object is to provide an electrophoretic support body and an electrophoretic device which allow a potential of hydrogen (pH) to be easily and reproducibly adjusted. The electrophoretic support body in the present disclosure is an electrophoretic support body including a plurality of fibers, the plurality of fibers form a fibrous body having a void in the fibrous body, and the plurality of fibers include a metal oxide having a predetermined isoelectric point. The electrophoretic device in the present disclosure includes a container, a pair of first electrodes provided in the container, and a first electrophoretic support body disposed between the pair of first electrodes, the first electrophoretic support body includes a fibrous body that is formed of a plurality of fibers and has a void in the fibrous body, and the plurality of fibers include a metal oxide having a predetermined isoelectric point.

21 Claims, 8 Drawing Sheets

(56) References Cited

U.S. PATENT DOCUMENTS

| | | | |
|---|---|---|---|
| 6,638,408 B1 * | 10/2003 | Speicher .......... | G01N 27/44747 |
| | | | 204/418 |
| 2009/0308811 A1 | 12/2009 | Tepper et al. | |
| 2014/0374260 A1 * | 12/2014 | Ohki ................ | G01N 27/44778 |
| | | | 204/610 |

FOREIGN PATENT DOCUMENTS

| | | |
|---|---|---|
| JP | 2005-084047 | 3/2005 |
| WO | 2009/152291 A1 | 12/2009 |
| WO | 2013/146199 | 10/2013 |

OTHER PUBLICATIONS

International Search Report of PCT application No. PCT/JP2016/001735 dated Jun. 21, 2016.
The Extended European Search Report dated Feb. 1, 2018 for the related European Patent Application No. 16776275.6.
English Translation of Chinese Search Report dated Mar. 6, 2019 for the related Chinese Patent Application No. 201680019918.8.

* cited by examiner mbox# ELECTROPHORETIC SUPPORT BODY AND ELECTROPHORETIC DEVICE This application is a U.S. national stage application of the PCT International Application No. PCT/JP2016/001735 filed on Mar. 25, 2016, which claimed the benefit of foreign priority of Japanese patent applications 2015-080490 and 2015-245853 filed on Apr. 10, 2015 and Dec. 17, 2015, respectively, the contents all of which are incorporated herein by reference.

FIELD OF THE INVENTION

The present disclosure relates to an electrophoretic support body and an electrophoretic device that are used for analyzing samples such as protein.

DESRIPTION OF THE RELATED ART

Electrophoresis is used as a technique of separating and analyzing samples such as deoxyribonucleic acid (DNA) and protein. Electrophoresis separates samples according to a difference in molecular weight or isoelectric point of the samples. For example, isoelectric point electrophoresis is a method for separating and analyzing samples utilizing a difference in isoelectric point of the samples. An electrophoretic device includes electrodes for applying an electric potential and an electrophoretic support body provided between the electrodes. Conventionally, the electrophoretic support body is formed of, for example, a glass nonwoven fabric or a poly-acrylamide gel.

As prior art literatures related to an invention of the present disclosure, Patent Literatures 1 and 2 are known, for example.

CITATION LIST

Patent Literatures

PTL 1: Unexamined Japanese Patent Publication No. 2004-361393
PTL 2: Unexamined Japanese Patent Publication No. 2005-84047

SUMMARY OF THE INVENTION

An electrophoretic support body has a predetermined potential of hydrogen (pH). There have been known some methods for adjusting the pH of the electrophoretic support body. With a conventional method, however, it is difficult to reproducibly adjust the pH of the support body. An object of the present disclosure is to provide an electrophoretic support body whose pH can be easily and reproducibly adjusted.

The electrophoretic support body of the present disclosure is an electrophoretic support body including a plurality of fibers, the plurality of fibers form a fibrous body having a void in the fibrous body, and the plurality of fibers include a metal oxide having a predetermined isoelectric point.

An electrophoretic device of the present disclosure includes a container, a pair of first electrodes provided in the container, and a first electrophoretic support body disposed between the pair of first electrodes, the first electrophoretic support body includes a fibrous body that is formed of a plurality of fibers and has a void in the fibrous body, and the plurality of fibers include a metal oxide having a predetermined isoelectric point.

With the electrophoretic support body and the electrophoretic device of the present disclosure, it is possible to easily and reproducibly adjust the pH of the electrophoretic support body.

DETAILED DESCRIPTION OF THE PREFERRED EMBODIMENTS

Figure 1:
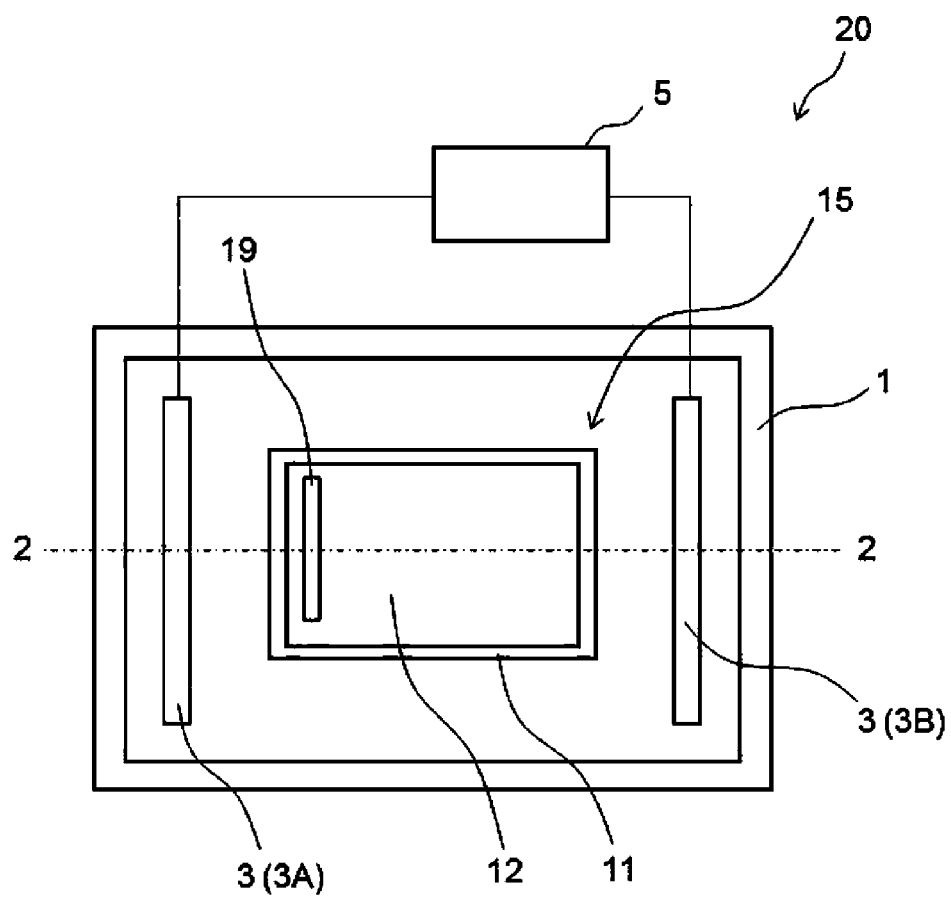
FIG. 1 is a top view schematically illustrating an electrophoretic device according to a first exemplary embodiment.

Prior to description of the present disclosure, problems of an electrophoretic device including a conventional electrophoretic support body are described as follows.

Electrophoresis is a phenomenon in which charged particles of a sample move when a voltage is applied to a pair of electrodes that are inserted in an analysis solution containing the sample. The sample moves through a void included in the electrophoretic support body. In the movement, the sample moves through the void at a different speed according to molecular weight of the sample. Therefore, a plurality of samples are separated according to a difference in movement distance during a voltage application period. In addition, a sample moves through the void to a position where the sample is equipotent to the electrophoretic support body according to a charge amount of the sample. Therefore, samples are separated according to a difference in isoelectric point.

In the electrophoresis, it is important to control pH of the electrophoretic support body. The pH of the electrophoretic support body affects the movement of a sample. For example, in electrophoresis of protein, the pH of the electrophoretic support body affects, for example, movement speed of protein. Accordingly, it is required to reproducibly control a pH condition of the electrophoretic support body for accurately performing the electrophoresis.

Further, an electrophoretic support body having a pH gradient is used for isoelectric point electrophoresis. As a method for forming a pH gradient in an electrophoretic support body, there is a method for adding a carrier ampholite and applying a voltage during electrophoresis. The method, however, has a problem that the pH gradient of the electrophoretic support body is unstable and less reproducible. As another method for forming a pH gradient in an electrophoretic support body, there is a method for disposing acidic or basic acrylamide derivatives in a poly-acrylamide gel and thus forming a pH gradient in the gel in advance. The method, however, has a problem that preparation of the gel is complicated and productivity is low.

Further, the electrophoretic support body including a gel is required to maintain a certain amount of moisture to keep a gel state and a void structure of the gel. Therefore, storage of the electrophoretic support body including a gel requires use of a package for keeping moisture. Furthermore, it is difficult to downsize the electrophoretic support body including a gel in terms of drying.

Hereinafter, an electrophoretic support body and an electrophoretic device according to exemplary embodiments of the present disclosure are described in detail with reference to drawings. It should be noted that the exemplary embodiments described below each illustrate one specific preferable example of the present disclosure. Therefore, a value, a shape, a material, a constituent, disposition and a connected state of a constituent, and the like illustrated in the following exemplary embodiments are one example and are not intended to limit the present disclosure. Accordingly, among the constituents in the following exemplary embodiments, a constituent that is not described in an independent claim indicating a most superordinate concept of the present invention is to be described as an optional constituent.

In addition, the drawings are schematic views that do not always illustrate exactly. In the drawings, the same reference mark is applied to the substantially same structure to omit or simplify duplicate description.

First Exemplary Embodiment

An electrophoretic device and an electrophoretic support body according to one aspect of the present disclosure are described with reference to FIGS. 1 to 3.

Figure 2:
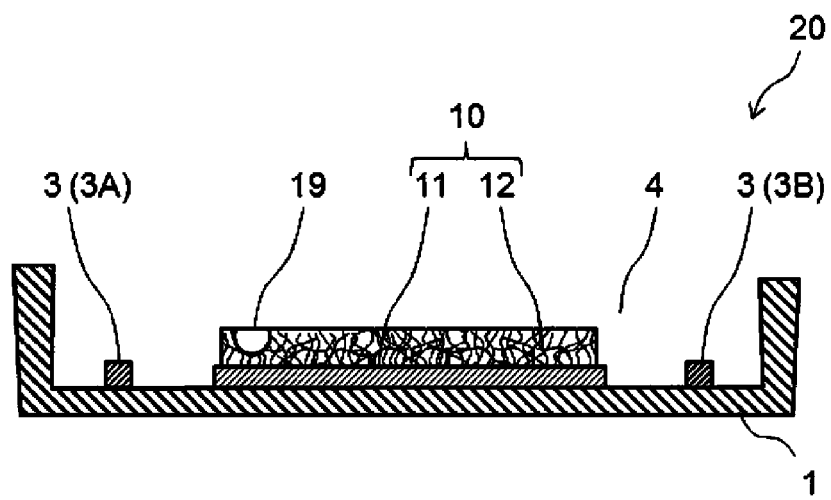
FIG. 2 is a sectional view schematically illustrating the electrophoretic device according to the first exemplary embodiment.

FIG. 1 is a top view of electrophoretic device 20. FIG. 2 is a sectional view taken along line 2-2 of electrophoretic device 20 illustrated in FIG. 1.

Electrophoretic device 20 includes container 1, electrophoretic support body 15, and electrodes 3.

Electrophoretic device 20 separates samples utilizing a difference in isoelectric point or molecular weight of the samples. The samples are, for example, protein and DNA.

Container 1 includes recess 4 on an upper surface of the container. Recess 4 is filled with a liquid such as a buffer solution during electrophoresis. Therefore, side walls of container 1 that form recess 4 are provided so as not to spill the liquid. A material of container 1 is, for example, a polymer such as a resin or silicon, or metal. Container 1 is formed by injection molding or cutting according to the material of the container. The material of container 1 is preferably a material that does not affect electrophoresis. In recess 4 of container 1, electrophoretic support body 15 and electrodes 3 are provided.

It should be noted that when a small amount of samples is used, the samples can be retained on an upper surface of container 1 by surface tension of the samples. Therefore, container 1 does not necessarily include recess 4.

Figure 3:
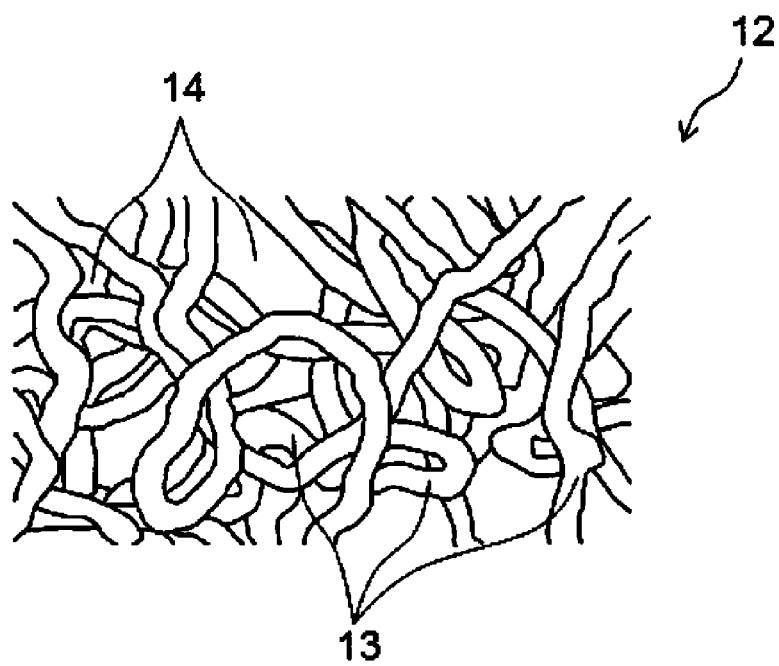
FIG. 3 is an enlarged view schematically illustrating a part of an electrophoretic support body according to the first exemplary embodiment.

FIG. 3 is an enlarged view of fibrous body 12 of electrophoretic support body 15.

Electrophoretic support body 15 includes substrate 11 and fibrous body 12 provided on substrate 11. Fibrous body 12 is formed of a plurality of fibers 13 that are entangled. Fibrous body 12 is a porous body. Fibrous body 12 has, in fibrous body 12, void 14 formed by entanglement of the plurality of fibers 13. In electrophoresis, the samples move through void 14 formed in fibrous body 12.

The plurality of fibers 13 that form fibrous body 12 include a metal oxide. Examples of the metal oxide included in fibers 13 include $SnO_2$, $ZnO$, $In_2O_3$, $Fe_3O_4$, $NiO$, $CuO$, $TiO_2$, and $SiO_2$.

The metal oxide has an isoelectric point dependent on a material of the metal oxide in a liquid.

For example, fibers 13 including $SiO_2$ have an isoelectric point of around pH 2. Therefore, fibrous body 12 that is formed of fibers 13 including $SiO_2$ has an isoelectric point of around pH 2. Fibers 13 including ZnO have an isoelectric point ranging, for example, from around pH 9 to around pH 10. Therefore, fibrous body 12 that is formed of fibers 13 including ZnO has an isoelectric point ranging from around pH 9 to around pH 10. As described above, when fibrous body 12 is formed of fibers 13 including only one metal oxide, fibrous body 12 has the same isoelectric point as the isoelectric point of the metal oxide. It should be noted that the plurality of fibers 13 that include metal oxides different in isoelectric point may be entangled to form fibrous body 12. The plurality of fibers 13 that have different isoelectric points can be mixed to form fibrous body 12 for fine adjustment of the isoelectric point of fibrous body 12.

A size of void 14 of fibrous body 12 can be easily adjusted by changing density of fibers 13. For example, as the density of fibers 13 increases, the size of void 14 decreases. The size of void 14 of fibrous body 12 is determined according to sizes of samples to be subjected to electrophoresis.

Fibers 13 are formed by, for example, a VSD (Vaporized Substrate Deposition) method or a VLS (Vapor Liquid Solid) method.

Hereinafter, a method for producing fibers 13 that include silicon dioxide as a main component is described.

When fibers 13 are prepared from silicon dioxide by the VSD method, used are an oxidizable gas such as oxygen or ozone and a material including silicon as a main component.

A silicon substrate is subjected to a heat treatment under conditions of a high temperature ranging from 900° C. to 1500° C. both inclusive, and low oxygen concentration. With this procedure, silicon of the substrate is vaporized. The vaporized silicon is bound to the oxidizable gas to form silicon monoxide. Subsequently, the silicon monoxide reattaches to a surface of the substrate to aggregate. In a process of aggregation, the silicon monoxide is bound to the oxidizable gas to form silicon dioxide. At this time, the silicon monoxide uniformly outspreads on a surface of silicon of the substrate. The silicon monoxide, however, selectively reattaches to a place where a catalyst layer is formed on the substrate. Therefore, in the place where the catalyst layer is formed, fibers 13 grow that include a silicon dioxide component as a main component.

Here, the low oxygen concentration means that an oxygen partial pressure is low during the heat treatment. For example, an environment of the heat treatment is a pressure-reduced state in which a pressure in an atmosphere is made lower than an atmospheric pressure. Alternatively, an oxygen gas in the atmosphere during the heat treatment may be replaced with another gas. The other gas is, for example, nitrogen, argon, and carbon monoxide. These gases are less oxidizable than oxygen or ozone. It should be noted that a low oxygen partial pressure is less likely to cause generation of silicon monoxide. Therefore, the oxygen partial pressure desirably ranges from $10^{-2}$ Pa to several thousand Pa.

Fibers 13 including silicon dioxide that are formed as described above have an amorphous structure. Fibers 13 have no specific crystalline structure, and therefore randomly grow. Therefore, fibers 13 are a winding shape that has a plurality of bent portions. Further, one fiber of fibers 13 formed is three-dimensionally and irregularly entangled with another fiber of fibers 13 in a growing process. As described above, the plurality of fibers 13 are entangled in the growing process of fibers 13 to form fibrous body 12. One fiber of fibers 13 may have a plurality of branching portions. That is, one fiber of fibers 13 is branched into two or more fibers 13 at a branching portion. Fibers 13 that are branched are entangled to make fibrous body 12 a strong structure.

Fibers 13 including a metal oxide other than silicon dioxide are formed by the method described above or another suitable method.

For example, the VLS method is a method of supplying a desired metal raw material and an oxygen gas in presence of a metal catalyst at a temperature ranging from about 200° C. to about 1300° C. both inclusive, to cause crystal growth directly under the metal catalyst. This method enables formation of fibers 13 that are a single crystal.

It should be noted that fibers 13 are not necessarily entangled with each other. For example, fibers 13 may be a straight shape. Alternatively, fibers 13 may be formed perpendicularly to substrate 11. In this case, fibrous body 12 is an aggregate of fibers 13 that is made of substantially the same material. Void 14 of fibrous body 12 means a gap between one fiber and another fiber of fibers 13.

It should be noted that in electrophoretic support body 15, substrate 11 may be a bottom surface of recess 4 included in container 1. It should be noted that in cases where only fibrous body 12 can hold a shape as electrophoretic support body 15, substrate 11 is not necessarily provided.

Electrodes 3 are provided on both end sides of electrophoretic support body 15. That is, anode 3A is provided at one end portion of electrophoretic support body 15. On the other hand, cathode 3B is provided at another end portion of electrophoretic support body 15. As a material of electrodes 3, there can be used, for example, conductive materials such as gold, platinum, copper, carbon, and a complex of these elements. A distance between electrodes 3 ranges, for example, from 5 mm to 2 cm both inclusive. Power supply apparatus 5 is connected to electrodes 3.

Power supply apparatus 5 controls a voltage applied between anode 3A and cathode 3B and an application period.

Hereinafter, an action of electrophoretic device 20 is described.

A buffer solution is injected into container 1 in which electrophoretic support body 15 is disposed. As the buffer solution, for example, PBS (Phosphate Buffered Saline) is used. Next, samples are injected into end portion 19 of electrophoretic support body 15. Subsequently, a predetermined voltage is applied between electrodes 3 by power supply apparatus 5. For example, a voltage of 500 V is applied between electrodes 3 for one minute. Subsequently, a voltage value is raised to 3500 V over one and a half hours. Further subsequently, a voltage of 3500 V is applied between electrodes 3 over six and a half hours. Application of a voltage forms an electric field between electrodes 3. Therefore, the samples move through electrophoretic support body 15. In the movement, a movement distance and a movement speed of the samples are different according to a difference in molecular weight and isoelectric point of the samples. Therefore, the samples are separated in electrophoretic support body 15 after electrophoresis. It should be noted that electrophoretic device 20 may be subjected to a stationary treatment before the samples are injected.

After the samples are separated, electrophoretic support body 15 is dyed to allow detection of positions of the samples separated. For dyeing electrophoretic support body 15, for example, silver stain is used. Alternatively, the samples may be dyed by a fluorescent pigment before electrophoresis. In this case, electrophoretic support body 15 that has undergone electrophoresis is irradiated with excitation light and fluorescence is observed to detect positions of the samples separated. As another method, the detection of the samples may be performed by using a method of irradiating electrophoretic support body 15 with light such as ultraviolet light or near-infrared light and detecting transmitted light or reflected light of the light radiated. Samples such as protein and DNA have characteristics of absorbing light having a specific wavelength. Therefore, in the detection of light that has irradiated electrophoretic support body 15, strength of light detected is weaker at places where the samples are located than at other places. Thus, the positions of the samples can be detected.

First Modified Example

Figure 4:
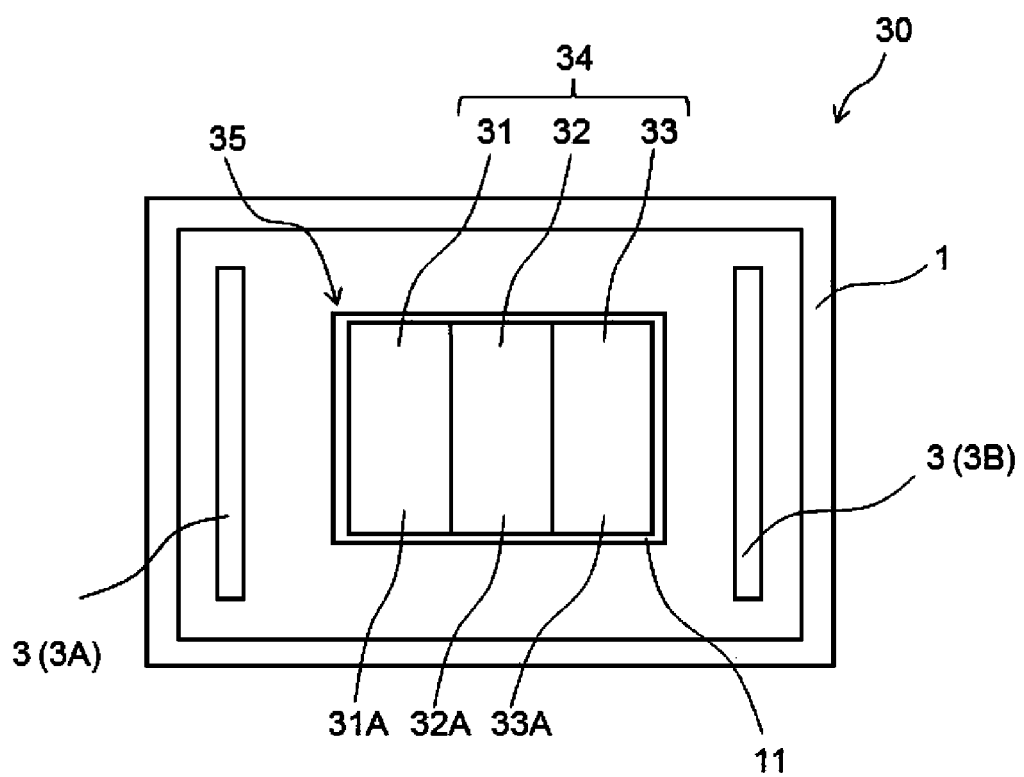
FIG. 4 is a top view schematically illustrating an electrophoretic device according to a first modified example of the first exemplary embodiment.

With reference to FIG. 4, electrophoretic device 30 according to a present modified example of the first exemplary embodiment is described.

FIG. 4 is a top view of electrophoretic device 30 according to the present modified example.

Electrophoretic device 30 disclosed in the present modified example includes as electrophoretic support body 35 a plurality of fibrous bodies 34 different in pH. In the following description, differences from the first exemplary embodiment are mainly described. As to a common matter, a same reference mark is applied and detailed description of the common matter is omitted.

Electrophoretic device 30 includes container 1 having recess 4, electrophoretic support body 35 disposed in recess 4, and electrodes 3.

Electrophoretic support body 35 includes first fibrous body 31, second fibrous body 32, and third fibrous body 33. First fibrous body 31 is formed of first fiber 31A. Second fibrous body 32 is formed of second fiber 32A. Third fibrous body 33 is formed of third fiber 33A. First fibrous body 31, second fibrous body 32, and third fibrous body 33 each include a void in the fibrous body. First fiber 31A, second fiber 32A, and third fiber 33A include materials each having a different isoelectric point. With this configuration, first fibrous body 31, second fibrous body 32, and third fibrous body 33 each have a different isoelectric point.

Further, the isoelectric point of first fibrous body 31 is smaller than the isoelectric point of second fibrous body 32. Furthermore, the isoelectric point of second fibrous body 32 is smaller than the isoelectric point of third fibrous body 33. As described above, the plurality of fibrous bodies 34 are disposed so as to line in ascending order of the isoelectric point from an anode 3A end to a cathode 3B end in electrophoretic support body 35. Specifically, for example, first fibrous body 31 is formed of first fiber 31A including $SiO_2$. Second fibrous body 32 is formed of second fiber 32A including $SnO_2$. Third fibrous body 33 is formed of third fiber 33A including ZnO. Therefore, in electrophoretic support body 35, first fibrous body 31 having an isoelectric point of pH 2, second fibrous body 32 having an isoelectric point of pH 7, and third fibrous body 33 having an isoelectric point of pH 9 are lined in this order. Accordingly, electrophoretic support body 35 has a pH gradient.

It should be noted that the plurality of fibrous bodies 34 included in electrophoretic support body 35 may be further increased. Fibrous bodies 34 different in isoelectric point can be increased to finely adjust the pH gradient of electrophoretic support body 35. For example, fibrous bodies 34 may be disposed from pH 2 to pH 12 with pH 1 increments in between. Fibrous bodies 34 are each formed of a metal oxide fiber having a predetermined isoelectric point.

The electrophoretic support body having a pH gradient can be used for, for example, isoelectric point electrophoresis.

Second Modified Example

Figure 5:
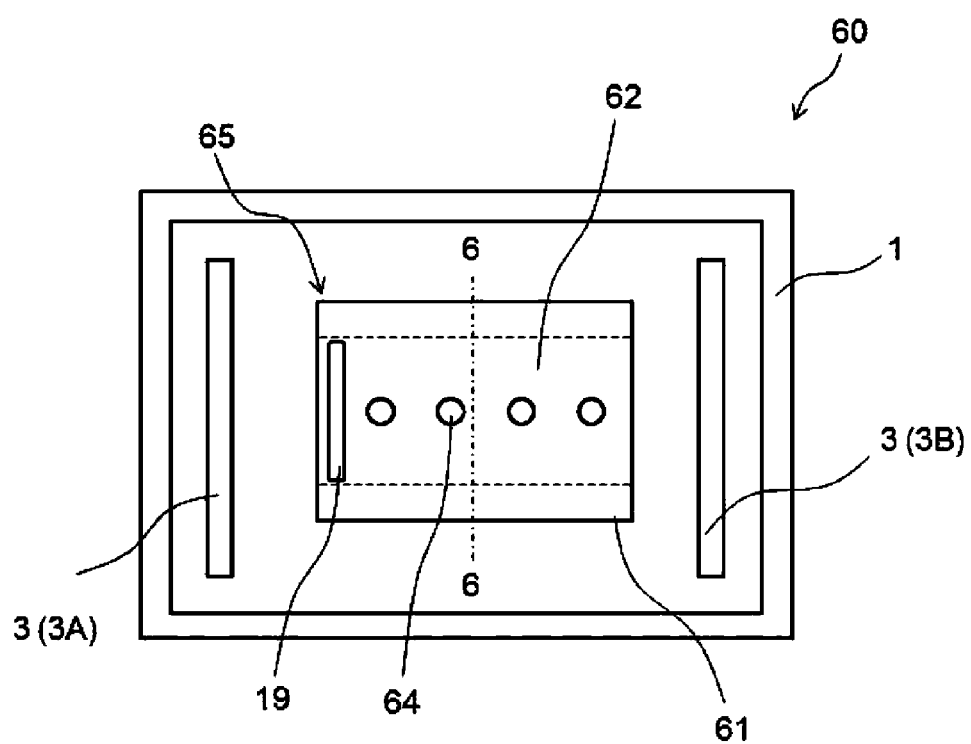
FIG. 5 is a top view schematically illustrating an electrophoretic device according to a second modified example of the first exemplary embodiment.
Figure 6:
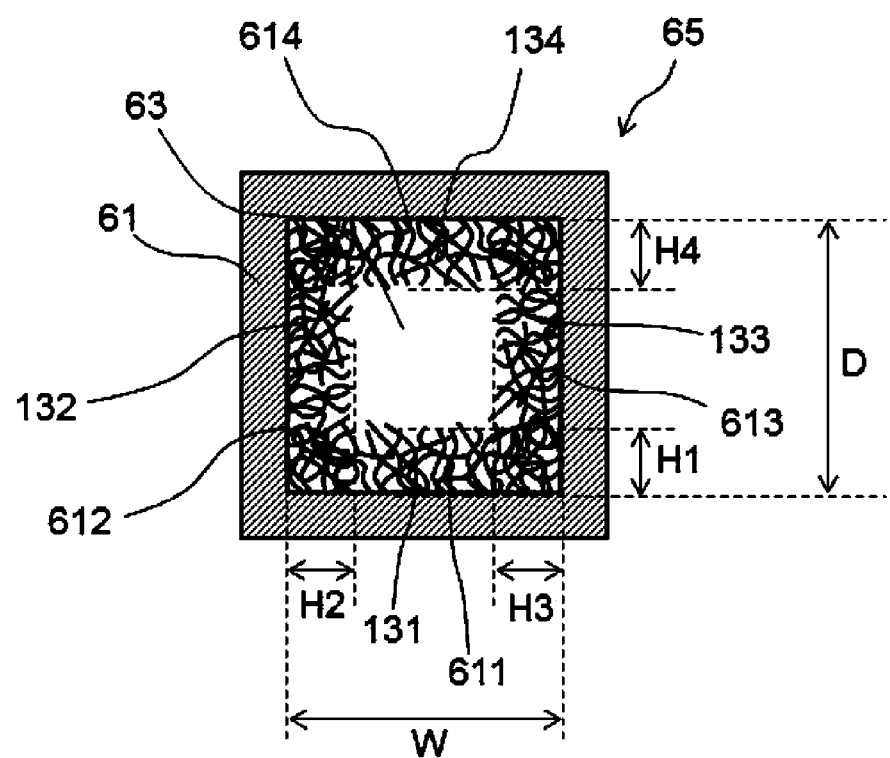
FIG. 6 is a sectional view schematically illustrating an electrophoretic support body according to the second modified example of the first exemplary embodiment.
Figure 7:
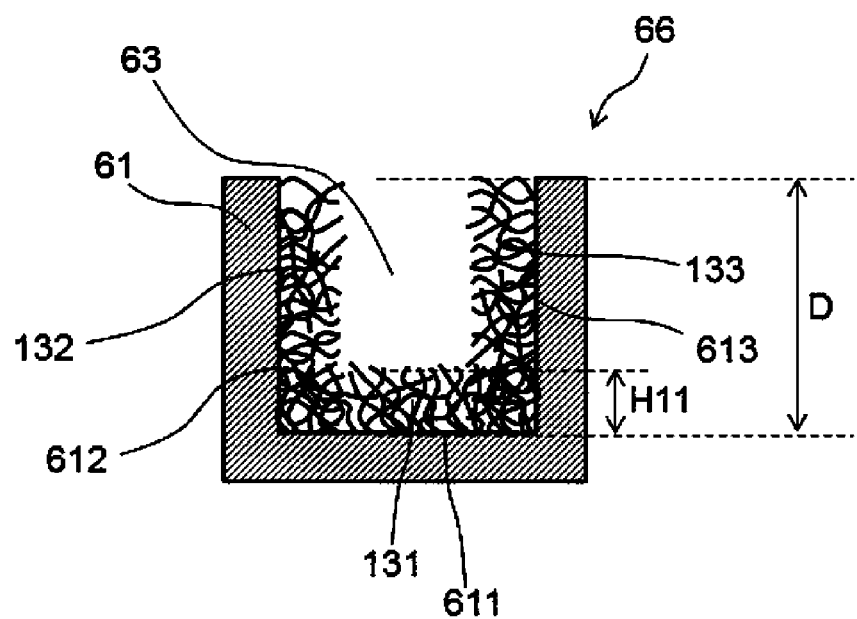
FIG. 7 is a sectional view schematically illustrating another example of the electrophoretic support body according to the second modified example of the first exemplary embodiment.

With reference to FIGS. 5 to 7, electrophoretic device 60 according to a present modified example of the first exemplary embodiment is described. In the following description, differences from the first exemplary embodiment are mainly described. As to a common matter, a same reference mark is applied and detailed description of the common matter is omitted.

FIG. 5 is a top view of electrophoretic device 60 according to the present modified example. FIG. 6 is a sectional view schematically illustrating a section taken along line 6-6 in electrophoretic support body 65 according to the present modified example in FIG. 5.

Electrophoretic support body 65 disclosed in the present modified example includes substrate 61 that is cylindrical. Substrate 61 includes flow channel 62 surrounded by bottom surface 611, first side surface 612, second side surface 613, and upper surface 614. Samples pass through flow channel 62. It should be noted that substrate 61 may be formed of a lower member in which a groove is formed and a lid member.

On inner wall surfaces of substrate 61 that form flow channel 62 are disposed fourth to seventh fibrous bodies 131 to 134 that are each an aggregate of a plurality of fibers 13. Fourth fibrous body 131 is disposed on bottom surface 611. Fifth fibrous body 132 is disposed on first side surface 612. Sixth fibrous body 133 is disposed on second side surface 613. Seventh fibrous body 134 is disposed on upper surface 614. The plurality of fibers 13 included in fourth to seventh fibrous bodies 131 to 134 are made from a same material.

Here, fourth fibrous body 131 is isolated from seventh fibrous body 134. That is, a sum of height H1 of fourth fibrous body 131 and height H4 of seventh fibrous body 134 is smaller than depth D of flow channel 62. With this configuration, space 63 where fibers 13 are not disposed is formed between fourth fibrous body 131 and seventh fibrous body 134. In addition, fifth fibrous body 132 is isolated from sixth fibrous body 133. That is, a sum of height H2 of fifth fibrous body 132 and height H3 of sixth fibrous body 133 is smaller than width W of flow channel 62. With this configuration, space 63 where fibers 13 are not disposed is formed between fifth fibrous body 132 and sixth fibrous body 133.

In the present exemplary embodiment, it has been described that a solution around fibrous body 12 has a pH dependent on a material of a metal oxide. Here, pH characteristics in the solution dependent on a material of a metal oxide are generated stably at a tip portion of fibers 13. That is, the pH in the solution dependent on a metal oxide is stably generated in a region including a boundary between fibrous body 12 and space 63.

Therefore, in order to efficiently separate samples by electrophoresis, it is effective to increase an area of a boundary between fibrous body 12 and space 63.

In electrophoretic support body 65 illustrated in the present modified example, fourth to seventh fibrous bodies 131 to 134 are formed not only on bottom surface 611 but also on first side surface 612, second side surface 613, and upper surface 614, respectively. Further, fifth fibrous body 132 disposed on first side surface 612 is isolated from sixth fibrous body 133 disposed on second side surface 613. In addition, fourth fibrous body 131 disposed on bottom surface 611 is isolated from seventh fibrous body 134 disposed on upper surface 614. That is, fourth to seventh fibrous bodies 131 to 134 are disposed so as to form space 63 in flow channel 62.

Such a configuration can widen a boundary portion between space 63 and fibrous body 12 in electrophoretic support body 65. Therefore, electrophoretic support body 65 can separate many samples under a stable pH condition.

Further, electrophoretic support body 65 may have a plurality of through-holes 64 on upper surface 614. With the plurality of through-holes, electrophoretic support body 65 can facilitate operation of pouring, for example, a buffer solution to samples that have undergone electrophoresis.

It should be noted that electrophoretic support body 66 does not necessarily include upper surface 614 as illustrated in FIG. 7. With upper surface 614 not being provided, electrophoretic support body 66 can facilitate operation of, for example, pouring a buffer solution to samples that have undergone electrophoresis.

In this case, height H11 of fourth fibrous body 131 disposed on bottom surface 611 is smaller than depth D of flow channel 62. Therefore, space 63 can be formed above fourth fibrous body 131 disposed on bottom surface 611 in flow channel 62 of electrophoretic support body 66.

It should be noted that height H11 of fourth fibrous body 131 is preferably smaller than a half of depth D of flow channel 62. This configuration can widen an area of a boundary between fifth fibrous body 132 and space 63 and an area of a boundary between sixth fibrous body 133 and space 63.

When a small amount of a sample is used, however, the electrophoretic support body preferably includes upper surface 614 because the sample is vaporized.

Figure 8:
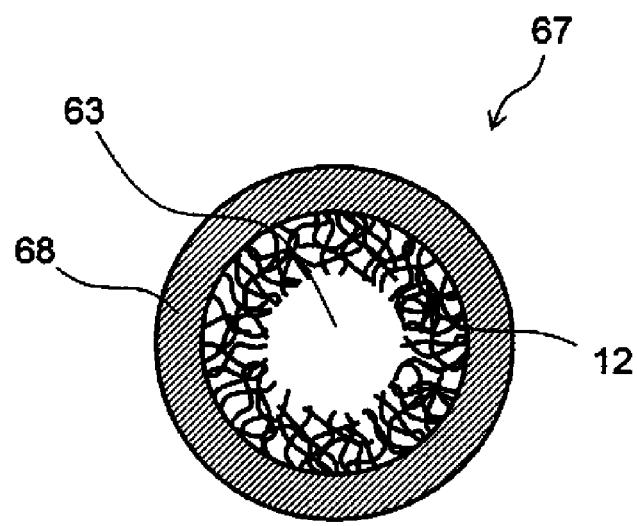
FIG. 8 is a sectional view schematically illustrating further another example of the electrophoretic support body according to the second modified example of the first exemplary embodiment.

Alternatively, as illustrated in FIG. 8, electrophoretic support body 67 may include substrate 68 that is a hollow cylinder, and fibrous body 12 disposed on an inner wall surface of substrate 68 that is a cylinder. In substrate 68 that is a cylinder, bottom surface 611, first side surface 612, second side surface 613, and upper surface 614 each indicate a part of an inner wall of substrate 68 that has a positional relationship relative to the surface.

Fibrous body 12 is disposed over entire circumference of an inner wall surface of substrate 68 that is a cylinder. Fibrous body 12 that is disposed on one part of the inner wall surface of substrate 68 is isolated from fibrous body 12 that is disposed on another part of the inner wall surface opposite to the one part of the inner wall surface, with a center of the cylinder interposed between the one part and the other part of the inner wall surface. That is, space 63 is formed where no fibers 13 are formed in the cylinder. Samples are separated according to a pH condition formed in space 63.

As described above, in electrophoretic support body 67, fibrous body 12 is disposed on the inner wall surface of substrate 68 that is a cylinder to enable control of the pH condition in a wider region in the cylinder. Therefore, electrophoretic support body 67 can efficiently separate more samples.

It should be noted that as described in the first modified example, electrophoretic support bodies 65, 66, 67 of the present modified example may have a length-wise pH gradient.

As described above, with electrophoretic support bodies 15, 35, 65, 66, 67, it is possible to easily and reproducibly adjust the pH. Electrophoretic support bodies 15, 35, 65, 66, 67 do not include a gel. Therefore, storage of electrophoretic support bodies 15, 35, 65, 66, 67 do not require use of a package for keeping moisture. Further, electrophoretic support bodies 15, 35, 65, 66, 67 can be easily downsized.

Second Exemplary Embodiment

Figure 9:
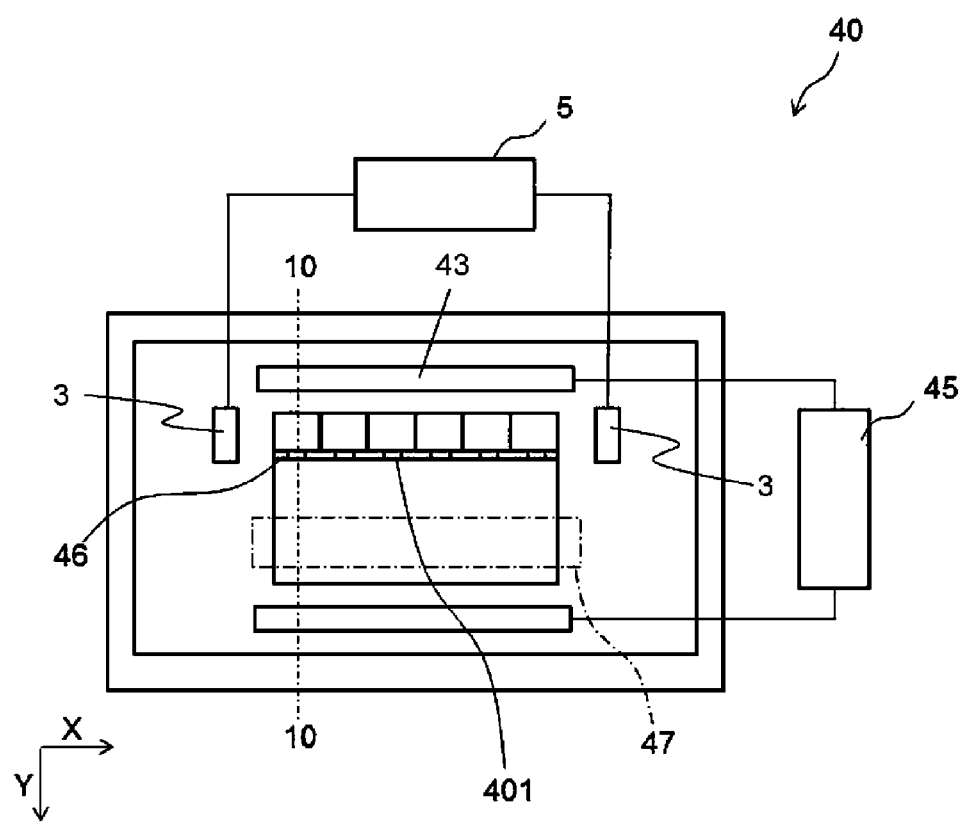
FIG. 9 is a top view schematically illustrating an electrophoretic device according to a second exemplary embodiment.
Figure 10:
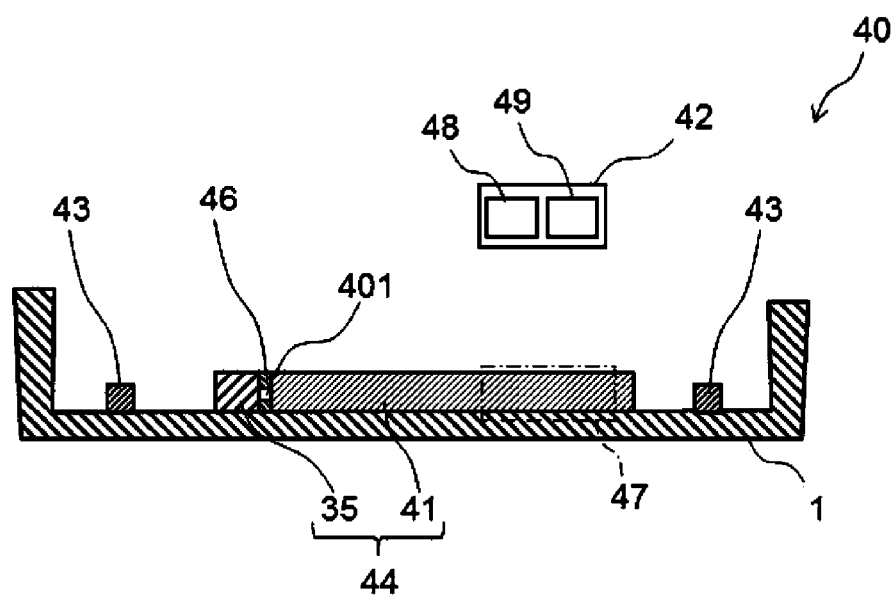
FIG. 10 is a sectional view schematically illustrating the electrophoretic device according to the second exemplary embodiment.

With reference to FIGS. 9 and 10, electrophoretic device 40 according to a present exemplary embodiment is described.

FIG. 9 is a top view of electrophoretic device 40 according to the present exemplary embodiment. FIG. 10 is a sectional view taken along line 10-10 of electrophoretic device 40 in FIG. 9.

Electrophoretic device 40 according to the present exemplary embodiment is used for two-dimensional electrophoresis. Electrophoretic device 30 disclosed in the first modified example of the first exemplary embodiment can be used for first-dimensional isoelectric point electrophoresis of the two-dimensional electrophoresis. In the following description, differences from the first exemplary embodiment are mainly described. As to a common matter, a same reference mark is applied and detailed description of the common matter is omitted.

Electrophoretic device 40 includes container 1 having recess 4, electrophoretic support body 44, electrodes 3, 43, power supply apparatuses 5, 45, and detector 42. Electrophoretic support body 44 includes first-dimensional electrophoretic support body 35 and second-dimensional electrophoretic support body 41.

The first-dimensional electrophoresis is an isoelectric point electrophoresis. As first-dimensional electrophoretic support body 35, electrophoretic support body 35 of the first modified example is used. In FIG. 6, first-dimensional electrophoretic support body 35 has a pH gradient formed by six fibrous bodies 34 different in isoelectric point.

Second-dimensional electrophoretic support body 41 is integrally joined with a side surface of first-dimensional electrophoretic support body 35. A direction of second-dimensional electrophoresis (Y-direction) is perpendicular to a direction of first-dimensional electrophoresis (X-direction). It should be noted that electrophoretic support body 35 and electrophoretic support body 41 may be disposed in the container so as to be directly or indirectly in contact with each other.

In the second-dimensional electrophoresis, samples are separated according to a difference in molecular weight of the samples. Second-dimensional electrophoretic support body 41 is electrophoretic support body 15 that is disclosed in the first exemplary embodiment and includes fibrous body 12, or an electrophoretic support body including a gel. When electrophoretic support body 15 including fibrous body 12 is used, electrophoretic support body 41 is desirably formed of one fibrous body 12. The electrophoretic support body including a gel is formed of, for example, an agarose gel or a polyacrylamide gel.

Hereinafter, an action of second-dimensional electrophoresis is described.

First-dimensional electrophoretic support body 35 holds a buffer solution. As the buffer solution, for example, PBS is used. The buffer solution is in contact with electrodes 3. At this time, the buffer solution does not preferably leak toward second-dimensional electrophoretic support body 41. It should be noted that electrophoretic support body 35 may be filled with the buffer solution in advance or directly before electrophoresis.

Next, samples are spotted to an end portion of first-dimensional electrophoretic support body 35. Subsequently, a predetermined voltage is applied between electrodes 3 by power supply apparatus 5. For example, a voltage of 500 V is applied between electrodes 3 for one minute. Subsequently, a voltage value is raised to 3500 V over one and a half hours. Further subsequently, a voltage of 3500 V is applied between electrodes 3 over six and a half hours. A voltage is applied to form an electric field between electrodes 3. When the electric field is formed, the samples move through electrophoretic support body 35 until the samples each reach an isoelectric point where a charge of the sample becomes zero. Therefore, the samples are separated according to the isoelectric point of the samples in electrophoretic support body 35 that has undergone electrophoresis. It should be noted that electrophoretic device 40 may be subjected to a stationary treatment before the samples are spotted.

Subsequently, the samples that have been separated according to the isoelectric point by the first-dimensional electrophoresis are subjected to second-dimensional electrophoresis. A predetermined voltage is applied between electrodes 43 by power supply apparatus 45. For example, a voltage of 80 V is applied between electrodes 43 for 16 hours. By this application, the samples move through second-dimensional electrophoretic support body 41 in the Y-direction. In the second-dimensional electrophoresis, the samples are separated according to a difference in molecular weight of the samples.

It should be noted that second-dimensional electrophoretic support body 41 holds a buffer solution different from the buffer solution held by first-dimensional electrophoretic support body 35. The buffer solution held by second-dimensional electrophoretic support body 41 is PBS including SDS (Sodium Dodecyl Sulfate). It should be noted that partition 46 may be provided between first-dimensional electrophoretic support body 35 and second-dimensional electrophoretic support body 41. Partition 46 separates electrophoretic support body 35 from electrophoretic support body 41. Partition 46 is removed after the first-dimensional electrophoresis is completed. The partition never allows the buffer solution held by second-dimensional electrophoretic support body 41 to leak toward first-dimensional electrophoretic support body 35. Therefore, electrophoretic device 40 can accurately perform the first-dimensional electrophoresis.

It should be noted that partition 46 may have a plurality of through-holes 401 every pH of the pH gradient of first-dimensional electrophoretic support body 35. With the through-holes, it is possible to send the samples that have been separated by the first-dimensional electrophoresis to second-dimensional electrophoretic support body 41 without removing partition 46.

After the samples are separated by the second-dimensional electrophoresis, electrophoretic support body 41 is dyed. The dyeing enables detection of positions of the samples separated. For the dyeing of electrophoretic support body 41, for example, silver stain is used. Alternatively, the samples may be dyed by a fluorescent dye before electrophoresis. In this case, electrophoretic support body 41 that has undergone the electrophoresis is irradiated with excitation light and fluorescence is observed to detect positions of the samples. As another method, the detection of the samples may be performed by using a method of irradiating electrophoretic support body 41 with light such as ultraviolet light or near-infrared light and detecting transmitted light or reflected light of the light radiated. Samples such as protein and DNA have characteristics of absorbing light having a specific wavelength. Therefore, in detection of light that has irradiated electrophoretic support body 41, strength of light detected is weaker at places where the samples are located than at other places. Thus, the positions of the samples can be detected.

It should be noted that in the first-dimensional electrophoresis, electrophoretic support bodies 65, 66, 67 illustrated in the second modified example of the first exemplary embodiment may also be used. With use of an electrophoretic support body illustrated in the second modified example, second-dimensional electrophoretic support body 41 is joined with the second side surface of the electrophoretic support body of the second modified example with a part of the substrate interposed between the electrophoretic support bodies. Second side surface 612 in contact with second-dimensional electrophoretic support body 41 may have a plurality of through-holes to send the samples that have been separated by the first-dimensional electrophoresis to second-dimensional electrophoretic support body 41.

Figure 11:
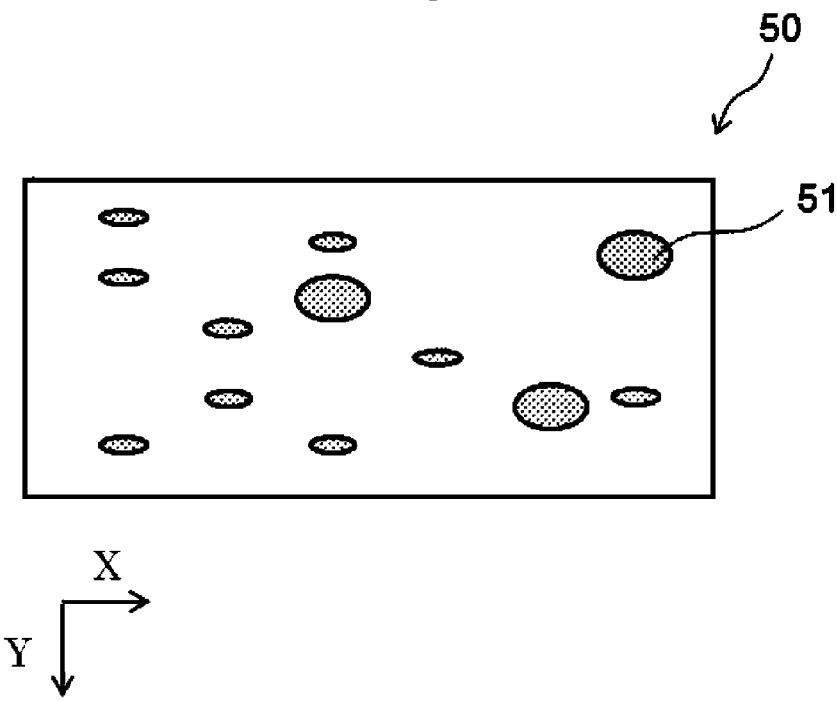
FIG. 11 is an imaginary view schematically illustrating a detected image of an electrophoretic support body according to the second exemplary embodiment.

FIG. 11 is detected image 50 of second-dimensional electrophoretic support body 41 that has been dyed after separation of the samples.

In the detected image, detected places 51 are six columns in the X-direction. This indicates that the samples have been separated into 6 isoelectric points by the first-dimensional electrophoresis. Further, detected places 51 are distributed in the Y-axis direction in each of the columns. This indicates that the samples that have been separated according to the isoelectric point by the first-dimensional electrophoresis are separated according to the difference in molecular weight of the samples by the second-dimensional electrophoresis.

As described above, the samples are separated according to the isoelectric point and the molecular weight. At this time, with use of, for example, a molecular-weight marker, the samples detected can be identified. Alternatively, in cases where a result of second-dimensional electrophoresis for a specific sample exists as a reference image in advance, the detected image may be compared with the reference image to identify the sample analyzed.

It should be noted that as a method of acquiring a detected image, a sample may be detected during second-dimensional electrophoresis. For example, as illustrated in FIGS. 9 and 10, detector 42 is provided above detecting region 47 of the second-dimensional electrophoretic support body. Detector 42 includes irradiating device 48 for radiating light such as ultraviolet light and light receiving device 49 for receiving light. Detecting region 47 of detector 42 is a part of a length-wise (Y-axis direction) region and an entire width-wise (X-axis direction) region of second-dimensional electrophoretic support body 41. Detector 42 is fixed to, for example, electrophoretic device 40, so as not to change a relative position with second-dimensional electrophoretic support body 41.

Detector 42 detects the samples in electrophoretic support body 41 during electrophoresis by restructuring an electrophoretic pattern with use of light irradiating detecting region 47.

The light radiated by the irradiating device is reflected on electrophoretic support body 41. The light reflected is received by the light receiving device. Detector 42 acquires strength of the light received as time-series data. When a sample is included in electrophoretic support body 41, the light radiated is absorbed by the sample. Therefore, the strength of the reflected light received decreases.

The data acquired can be plotted in a graph to generate the detected image as illustrated in FIG. 11. Here, a vertical axis of the graph indicates time. A horizontal axis indicates a width-wise position in detecting region 47. In addition, a size of detected places 51 indicates information on light strength. The size of detected places 51 is, for example, a reciprocal number of the light strength.

It should be noted that when the detection is performed with use of transmitted light of light that has irradiated detecting region 47, irradiating device 48 and light receiving device 49 are provided at positions symmetrical to detecting region 47.

As described above, detected image 50 of the samples separated can be acquired during electrophoresis to shorten time of detecting the samples. It should be noted that information on light received is not limited to the power of light strength. For example, the information on light may be, for example, a frequency of light.

As described above, one form or a plurality of forms of the electrophoretic support body and the electrophoretic device have been described based on the exemplary embodiments. The present disclosure, however, is not limited to these exemplary embodiments. A range of the one form or the plurality of forms may include one obtained by applying various modifications that a person skilled in the art conceives to the present exemplary embodiments or a form constructed by combining constituents in different exemplary embodiments, without departing from a subject matter of the present disclosure.

The invention claimed is:

1. An electrophoretic support body comprising:
a first fibrous body including a plurality of first fibers, the first fibrous body having voids therein, the first fibrous body having a first isoelectric point; and
a second fibrous body including a plurality of second fibers, the second fibrous body having voids therein, the second fibrous body having a second isoelectric point,
wherein the plurality of first fibers includes a first metal oxide, and
the plurality of second fibers includes a second metal oxide different from the first metal oxide.

2. The electrophoretic support body according to claim 1, further comprising a third fibrous body including a plurality of third fibers, the third fibrous body having voids therein, the third fibrous body having a third isoelectric point, wherein
the plurality of third fibers include a third metal oxide different from the first and second metal oxides, and
the first, second and third fibrous bodies are disposed so as to line in ascending order of the respective isoelectric point from one end to another end of the electrophoretic support body.

3. An electrophoretic device comprising:
a container;
a pair of first electrodes provided in the container; and
a first electrophoretic support body disposed between the pair of first electrodes,
wherein the first electrophoretic support body is the electrophoretic support body according to claim 1.

4. The electrophoretic device according to claim 3, wherein
the first electrophoretic support body further includes a third fibrous body including a plurality of third fibers, the third fibrous body having voids therein, the third fibrous body having a third isoelectric point,
the plurality of third fibers includes a third metal oxide different from the first and second metal oxides, and
the first, second and third fibrous bodies are disposed so as to line in ascending order of the respective isoelectric point from one end to another end of the first electrophoretic support body.

5. The electrophoretic device according to claim 3, further comprising:
a pair of second electrodes provided in the container; and
a second electrophoretic support body disposed between the pair of second electrodes,
wherein
the second electrophoretic support body is integrally joined with a side surface of the first electrophoretic support body.

6. The electrophoretic device according to claim 5, further comprising a partition provided between the second electrophoretic support body and the first electrophoretic support body.

7. The electrophoretic device according to claim 5, further comprising a detector for receiving light that has irradiated a detecting region of the second electrophoretic support body,
wherein
the detector detects a sample moving through the second electrophoretic support body by restructuring an electrophoretic pattern with use of the light.

8. An electrophoretic support body, comprising:
a plurality of fibers; and
a substrate that includes a flow channel formed of a bottom surface, a first side surface, and a second side surface opposite to the first side surface,
wherein
the plurality of fibers form a fibrous body that has a void in the fibrous body,
the plurality of fibers includes a metal oxide that has a predetermined isoelectric point,
the fibrous body is disposed on the bottom surface, the first side surface, and the second side surface,
a height of the fibrous body disposed on the bottom surface is smaller than a depth of the flow channel, and
the fibrous body disposed on the first side surface is disposed so as to be separated from the fibrous body disposed on the second side surface.

9. An electrophoretic support body, comprising:
a plurality of fibers; and
a substrate that includes a flow channel formed of a bottom surface, a first side surface, and a second side surface opposite to the first side surface; and
a fibrous body disposed in the flow channel,
wherein
the plurality of fibers form a fibrous body that has a void in the fibrous body,
the plurality of fibers includes a metal oxide that has a predetermined isoelectric point,
the fibrous body is formed of the plurality of fibers that are entangled and is a porous body having a void among the plurality of fibers,
the fibrous body is disposed on the bottom surface, the first side surface, and the second side surface,
a height of the fibrous body disposed on the bottom surface is smaller than a depth of the flow channel, and
the fibrous body disposed on the first side surface is separated from the fibrous body disposed on the second side surface.

10. The electrophoretic support body according to claim 9, wherein
the substrate further includes an upper surface opposite to the bottom surface with the flow channel interposed between the upper surface and the bottom surface,
the fibrous body is disposed on the upper surface, and
the fibrous body disposed on the bottom surface is separated from the fibrous body disposed on the upper surface.

11. The electrophoretic support body according to claim 9, wherein
the substrate is a cylinder, and
the fibrous body is disposed on an entire circumference of an inner wall surface of the cylinder.

12. The electrophoretic support body according to claim 10, wherein the upper surface of the substrate further has a plurality of through-holes.

13. An electrophoretic device, comprising:
a container;
a pair of first electrodes provided in the container; and
a first electrophoretic support body disposed between the pair of first electrodes;
a pair of second electrodes provided in the container; and
a second electrophoretic support body disposed between the pair of second electrodes,
wherein
the first electrophoretic support body includes a fibrous body that is formed of a plurality of fibers and has a void in the fibrous body,
the plurality of fibers include a metal oxide that has a predetermined isoelectric point,
the first electrophoretic support body includes:
a substrate including a flow channel formed of a bottom surface, a first side surface, and a second side surface opposite to the first side surface; and
a fibrous body disposed in the flow channel,
wherein
the fibrous body is formed of a plurality of fibers that are entangled and is a porous body having a void among the plurality of fibers,
the fibrous body is disposed on the bottom surface, the first side surface, and the second side surface,
a height of the fibrous body disposed on the bottom surface is smaller than a depth of the flow channel,
the fibrous body disposed on the first side surface is separated from the fibrous body disposed on the second side surface,
the second electrophoretic support body is joined with the second side surface of the first electrophoretic support body with a part of the substrate interposed between the second electrophoretic support body and the first electrophoretic support body, and
the second side surface has a plurality of through-holes so as to connect the first electrophoretic support body to the second electrophoretic support body.

14. The electrophoretic support body according to claim 1, wherein an isoelectric point of the first metal oxide is different from an isoelectric point of the second metal oxide.

15. The electrophoretic device according to claim 3, wherein an isoelectric point of the first metal oxide is different from an isoelectric point of the second metal oxide.

16. The electrophoretic device according to claim 3, wherein the first fibrous body is directly connected to the second fibrous body.

17. The electrophoretic device according to claim 5, wherein the second electrophoretic support body is integrally joined with the first fibrous body and the second fibrous body of the first electrophoretic support body at the side surface of the first electrophoretic support body.

18. The electrophoretic support body according to claim 1, wherein an isoelectric point of the plurality of first fibers is different from an isoelectric point of the plurality of second fibers, so that the first isoelectric point is different from the second isoelectric point.

19. The electrophoretic support body according to claim 2, wherein an isoelectric point of the plurality of third fibers is different from the isoelectric point of the plurality of first fibers and the isoelectric point of the plurality of second fibers, so that the first isoelectric point is smaller than the second isoelectric point, and the second isoelectric point is smaller than the third isoelectric point.

20. The electrophoretic support body according to claim 3, wherein an isoelectric point of the plurality of first fibers is different from an isoelectric point of the plurality of second fibers, so that the first isoelectric point is different from the second isoelectric point.

21. The electrophoretic support body according to claim 4, wherein an isoelectric point of the plurality of third fibers is different from the isoelectric point of the plurality of first fibers and the isoelectric point of the plurality of second fibers, so that the first isoelectric point is smaller than the second isoelectric point, and the second isoelectric point is smaller than the third isoelectric point.

* * * * *